United States Patent
Chang

[11] Patent Number: 6,129,916
[45] Date of Patent: *Oct. 10, 2000

[54] METHOD OF INCREASING ACTIVATION ON PROLIFERATION OF T CELLS USING ANTIBODY-MICROBEAD CONJUGATES

[75] Inventor: Tse Wen Chang, Houston, Tex.

[73] Assignee: Tanox, Inc., Houston, Tex.

[*] Notice: This patent is subject to a terminal disclaimer.

[21] Appl. No.: 07/981,276

[22] Filed: Nov. 25, 1992

Related U.S. Application Data

[63] Continuation-in-part of application No. 07/926,566, Aug. 6, 1992, abandoned, and a continuation-in-part of application No. 07/819,449, Jan. 10, 1992, abandoned, which is a continuation-in-part of application No. 07/688,000, Apr. 19, 1991, abandoned.

[51] Int. Cl.[7] .................................................. A61K 39/40
[52] U.S. Cl. ...................... 424/179.1; 424/486; 424/485; 424/450; 424/178.1; 530/866; 530/402; 530/391.1; 530/388.22; 530/388.75; 530/389.6; 530/387.1; 436/536; 436/533; 436/530; 436/529; 436/524; 436/512
[58] Field of Search ............................ 530/388.75, 389.6, 530/387.1, 388.22, 391.1, 866, 402; 436/524, 529, 533, 530, 526, 512; 424/450, 485, 488, 85.8, 179.1, 178.1

[56] References Cited

FOREIGN PATENT DOCUMENTS

| | | |
|---|---|---|
| 3242389 | 5/1989 | Australia . |
| 6623590 | 5/1991 | Australia . |
| 0336379 | 4/1989 | European Pat. Off. . |
| WO8912458 | 12/1989 | WIPO . |
| WO9006758 | 6/1990 | WIPO . |
| WO9013281 | 11/1990 | WIPO . |
| WO9013316 | 11/1990 | WIPO . |
| WO9103493 | 3/1991 | WIPO . |
| WO9206193 | 4/1992 | WIPO . |
| WO9207878 | 5/1992 | WIPO . |
| WO9213562 | 8/1992 | WIPO . |

OTHER PUBLICATIONS

Paul, Fundamental Immunology 364 (1989).
Verwilghen et al Immunology 72:269 1991.
Geppert JI 138:1660 1987.
Martin et al JI 136:3282 1986.
Pharmacia LKB Biotechnology Products Catalog 1989 p. 244.
Williams et al JI 135:2249 1985.
Harlow et al Antibodies A Laboratory Manual 1988 Cold Spring Harbor Pours pp. 626–627 & 533.
Charon et al PNAS 78:7166 1981.
Harris et al TibTech 11:42 1993.
Kelly et al J Allergy Clin Immunol 91:1140–1145 1993.

*Primary Examiner*—Jyothsan Venkat
*Assistant Examiner*—T. D. Wessendorf
*Attorney, Agent, or Firm*—Eric P. Mirabel

[57] ABSTRACT

Disclosed are conjugates including a polymer backbone or microbead and binding molecules, such as Fv, Fab, or F(ab')$_2$ fragments of monoclonal antibodies or whole antibodies that are bound through their Fc carbohydrate moieties or have their Fc portion modified so that they cannot effect ADCC or complement-mediated cytolysis, and that are specific for a T cell surface antigen, such as CD3, TCR, CD4, CD8, or CD28 on T cells. The polymer or microbead is preferably made of cross-linked dextran, ficoll, latex, or agarose. The microbeads are preferably of 1 to 10 $\mu$m in size, so that they can be suspended in in vivo fluids. These conjugates can be used to induce proliferation of T cells and immune stimulation, and to increase the antibody response against an administered antigen.

5 Claims, No Drawings

METHOD OF INCREASING ACTIVATION ON PROLIFERATION OF T CELLS USING ANTIBODY-MICROBEAD CONJUGATES

RELATED APPLICATIONS

This application is a continuation-in-part of U.S. application Ser. No. 07/926,566, filed Aug. 6, 1992, now abandoned and U.S. application Ser. No. 07/819,449, filed Jan. 10, 1992, abandoned, which is a continuation-in-part of U.S. application Ser. No. 07/688,000, filed Apr. 19, 1991, now abandoned.

FIELD OF INVENTION

The invention relates to immunoconjugates for modulating the immune system by inducing specifically the polyclonal activation, proliferation, and/or lymphokine production of T lymphocytes, or subsets thereof.

BACKGROUND OF THE INVENTION

Most immune responses involve many components of the immune system. Although the immune mechanisms involved in the elimination of malignantly transformed cells are not well understood, it is reasonable to assume that if more immune mechanisms are activated and enhanced, the tumorous cells may be eliminated more effectively. Also, both humoral and cellular mechanisms are known to be involved in the immune response against viruses and virus-infected cells. Thus, generally speaking, for the therapeutic treatments of patients with various cancers or infectious diseases, and for protecting individuals exposed to infectious agents from contracting the infection, it is desirable to enhance the entire immune system.

The various branches of the immune system include antibodies, cytotoxic T cells (CTLs), T cells mediating delayed-type hypersensitivities ($T_{TDH}$ cells), monocytes and macrophages, natural killer (NK) cells, K cells mediating antibody dependent cellular cytotoxicity ("ADCC"), and granulocytes. Complex interactions are involved in the activation of these various branches. The helper T cells ($T_h$ cells) play central regulatory roles, and many factors are secreted by these cells and other cells in a certain concerted fashion during the activation and proliferation phases. There is good reason to believe that the concerted production of lymphokines and cytokines, at the appropriate time and in the proper relative proportions, is important for maximizing the immune response.

Potentiation of the immune system is desirable for treating a number of pathologic conditions, e.g., for treatment of malignant tumors. The immune potentiators include substances identified from screening natural sources, such as cultures of microorganisms, marine animals, herbs, or plants, as well as substances screened from large batteries of synthetic organic compounds.

One example of a substance from a natural source is muramyl dipeptide, which has been identified as the smallest structure from the cell wall of staphylococcal bacteria which still retains immune potentiating effects. Many analogues of muramyl dipeptide have been synthesized. Muramyl dipeptide and its analogues are macrophage activators, and have been tested and developed as therapeutic agents for tumors and as adjuvants for vaccines.

Other examples of immune potentiators derived from natural sources include double-stranded RNA and mismatched double-stranded RNA (also called Ampligen) which can induce interferon synthesis and other immune functions. These substances have also been tested for treating tumors and viral diseases, such as AIDS.

Immune potentiators may be applied to patients alone or in combination with surgery, irradiation, or chemotherapy. They may also be desirable for treating patients with viral infectious diseases or for protecting individuals, after exposure to viruses, from contracting infection. Immune potentiators may be useful as adjuvants for various vaccines for infectious diseases or cancers.

Recently, recombinant human lymphokines and cytokines have been produced by genetic engineering. Many such recombinant "biological response modifiers" are being tested for treatment of various cancers and infectious diseases. A few recombinant products, such as interleukin-2 (IL-2), $\alpha$-interferon, $\gamma$-interferon, granulocyte-colony stimulation factor and granulocyte/monocyte-colony stimulation factor (G-CSF, GM-CSF), have been approved in many countries for use against certain cancers and infectious diseases. For example, IL-2 is approved for treating patients with renal cell carcinoma; $\alpha$-interferon is approved for treating patients with hairy cell carcinoma or with hepatitis B infection; G-CSF and GM-CSF are approved for treating cancer patients receiving chemotherapy for the purposes of restoring lost neutrophils.

Individual recombinant lympholines, such as IL-2, IL-4, or $\gamma$-interferon can augment some aspects of the immune system, but function only against limited immunocyte targets and can only potentiate certain immune functions and not the entire immune system. They also probably function only over short ranges and in limited areas in vivo. Also, cytolines and lymphokines which are injected into patients are cleared rapidly through the kidneys. They likely will not be present in sufficiently high concentrations in the lymphoid system for long enough to achieve their desired immunological effects.

Of the various substances other than lymphokines or cytokines which have been studied for potentiating the immune system, most are suitable for in vivo use do not target or enhance the T cells directly. For example, muramyl dipeptide, and analogues thereof, primarily activate macrophages. Double-stranded RNA and mismatched double-stranded RNA mainly induce interferon production by a variety of cells.

A few naturally-derived protein substances are known to be potent T cell mitogens in culture in vitro, and have been used in studies to characterize and quantitate T cell activity. These substances include phytohemagglutinin A (PHA), concanavalin A (Con A), wheat germ agglutinin (WGA), and some other lectins, defined as carbohydrate-binding plant proteins. However, these T-cell mitogenic proteins, although very useful for in vitro studies, have poor specificity and therefore bind to almost all cell types. Because they are toxic and lack specificity, they are not effective for in vivo use as T cell potentiators.

In order to activate and expand lymphocytes to achieve satisfactory therapeutic effects while avoiding administering toxic substances, some groups have sought to activate and expand the T lymphocytes from patients in culture in vitro for a period of time under optimal conditions and then harvest the activated cells and inject them back into the same patients. In this so-called IL-2/LAK therapeutic regimen, used by the Biological Therapy Institute (Franklin, Tenn.) to treat patients with various cancers, the blood is first drawn from the patients and the mononuclear cells are isolated. See Rosenberg, S. A. et al., *N. Eng. J. Med.* 316:889 (1987). The cells are incubated in medium containing recombinant IL-2 for several weeks, and the activated and expanded T cells, which contain the lympholine-activated killer (LAK) cells, are harvested and injected into the patients.

A more recent, modified version of this IL-2/LAK therapy, known as autolymphocyte therapy (ALT) has been developed by Cellcor Therapies, Inc. in Boston, Mass. See Osband, M. E. et al., *Lancet* 335:994 (1990). The lymphocytes from renal cell carcinoma patients are taken six times. The first time, the lymphocytes are stimulated with antibodies specific for human CD3 antigen (anti-CD3) in vitro to produce lymphokines. The culture supernatant is collected after a few days of culturing, and the cells are discarded. Then, the second through the sixth time, the lymphocytes taken from the patients are incubated in the "autologous" lymphokines for a period of five days and the cells are harvested and injected into the same patients.

It is claimed that these approaches, involving in vitro lymphocyte stimulation and expansion, achieve beneficial responses in a portion of the treated patients. The major concern with these regimens is that the treatment is very tedious, expensive, and requires a sophisticated, specialized cell culture facility. The variation among cells or cultures from different patients requires demanding monitoring procedures. Also, lymphocyte cultures have very poor viability even under optimal conditions, meaning that during the culturing, large numbers of the cells will die. When large numbers of dead cells are injected into patients, this may actually burden the reticuloendothelial system (RES) and reduce its effectiveness in combating the tumor cells.

In summary, the clinical studies and approved routine uses of IL-2 and γ-interferon and of LAK or ALT therapies indicate that T cell activation and expansion can achieve therapeutic effects in some patients with cancers or infectious diseases. On the other hand, the results of these treatments suggest that the lymphokine treatments have certain deficiencies and the LAK and ALT treatments have some substantial drawbacks. An efficacious and feasible treatment may be achieved if these deficiencies can be eliminated.

A number of MAbs specific for CD3 on the surface of human T cells (pan T marker) are known to be very potent mitogens of human T cells in vitro, e.g., the MAb OKT3. Van Wauwe, J. P. et al., *J. Immunology* 124:2708 (1980); Chang, T. W. et al., *Proc. Natl. Acad. Sci. U.S.A.* 78:1805 (1981); MAb 64.1 Hansen, J. A. et al., *Leukocyte Typing: Human Leukocyte Differentiation Antigens Detected by Monoclonal Antibodies,* Eds. Bernard, A. et al. (Spring Verlag, N.Y., 1984). In medium containing only fetal calf serum and no human serum (and therefore no IgG), the anti-CD3 MAbs are much more potent than PHA or Con A in inducing T cell proliferation.

But the mitogenic effect of anti-CD3 requires both specific binding to the CD3 antigen and the presence of the Fc moiety of the antibody, as well as the presence of monocytes and macrophages. The best explanation for these results is that the Fc of the anti-CD3 MAbs binds to the Fc receptors on monocytes/macrophages, thereby aggregating the CD3 antigen on the T cell surface. Since CD3 is associated with the T cell antigen receptors, the aggregation of CD3 triggers the activation and proliferation of the T cells.

This explanation is supported by experiments which show that when the anti-human CD3 MAb is conjugated to Sepharose 4B beads or coated on the substratum plastic surface of culture wells, monocytes and macrophages are not needed to induce activation and proliferation of T cells. See Williams, J. M. et al., *J. Immunol.* 135:2249 (1985); Ceuppens, J. L. & Baroja, M. L., *J. Immunol.* 137:1816 (1986); Geppert, T. D. & Lipsky P. E., *J. Immunol.* 138:1660 (1987). Based on these experiments, it has been suggested that the solid-phase anti-CD3 MAb functions by aggregating the CD3 antigen on the T cell surface.

However, when anti-human CD3 is injected in vivo, the results are the opposite of the in vitro effects. OKT3 MAb, which is the first MAb ever approved for therapeutic use in vivo, is strongly immunosuppressive and is approved for use as an immunosuppressor for patients receiving kidney transplants. Ortho Multicenter Group Study, *N. Eng. J. Med.* 313:337 (1985). The injection of OKT3 causes rapid depletion of T cells from the circulation.

Administration of anti-CD3 monoclonal antibodies (or F(ab')$_2$ fragments thereof) to mice also causes T cell depletion. Hirsch, R. et al., *TRANSPLANTATION* 49:1117–23 (1990). This monoclonal antibody also caused weight loss, diarrhea, and decreased activity within 24 hours in all mice, and death of one-half of the mice it was administered to in 3 days. Hirsch, R. et al., id. at p. 1118, col. 1, paragraph 2. In another study it was observed that mice administered 40 μg of this anti-CD3 antibody seemed to develop more rapidly growing tumors. Ellenhorn, J. D. et al., *Science* 242:569–571 (1988) at p. 570, in explanation of FIG. 3. These observations are consistent with the observation that this antibody caused depletion of T cells.

Although the mechanism by which anti-CD3 causes this rapid depletion of T cells is not well understood, the best explanation is that anti-CD3 induces ADCC of the T cells, i.e., as the T cells coated by anti-CD3 circulate through the spleen and liver, they are lysed by the phagocytic cells of the RES in these organs. It is also possible that some of the T cells are destroyed by complement-mediated cytolysis and some other cytolytic mechanisms. Thus, it is expected that conjugates of the OKT3 MAb with other substances will also cause depletion of T cells in vivo.

SUMMARY OF THE INVENTION

The immunoregulatory substances of the invention include conjugates including a polymeric backbone, such as latex, polyethylene glycol ("PEG"), cellulose, dextran, ficoll, agarose, an amino acid copolymer, a liposome, or a microbead that is coupled with binding molecules, for example, antibodies or antibody-derived fragments, e.g., Fv, Fab, or F(ab')$_2$, which bind to monovalent antigenic epitopes on CD3, epitopes of the T cell receptor, or other antigens on the surface of T cells, e.g., CD2, CD4, CD5, CD8, or CD28, or wherein at least one of the binding molecules specifically targets one of the antigens on T cells, e.g., CD2, CD3, CD4, CD5, CD8, CD28, or an epitope of the T cell receptor, and other binding molecule(s) specifically target the same antigen or other antigens or epitopes on T cells. The binding molecules either lack an Fc portion or have a modified Fc portion, or are bound to the polymer backbone or microbead, in such a way that the binding molecule is substantially ineffective in mediating antibody-dependent cellular cytotoxicity or complement-mediated cytolysis of T cells.

The immunoregulatory substances of the invention are specific for a surface antigen of T cells or subsets thereof. These antigens include: CD3, idiotype bearing receptor chains and other T cell receptor (TCR)-linked components; CD2, CD4, CD5, CD8, and other T cell-specific surface components. Many of these antigens contain only a single binding site for each MAb (i.e., a monovalent antigenic epitope).

The main use for the immunoregulatory substances is as immune potentiators which activate and expand T cells or a subset of the T cells, and stimulate them to produce IL-2, -γ-interferon, IL-1, IL-4, IL-6, tumor necrosis factor (TNF), or other lymphokines. Because T cells play central roles in the regulation of many branches of the immune system, the concerted secretion of a number of lymphokines will activate many immune mechanisms, whereas the administration of individual lymphokines will have a more limited effect.

Such immune potentiators may be used to treat patients with cancers or infectious diseases, or to protect individuals exposed to infectious agents from contracting the infections. Immune potentiators may also be applied as adjuvants for vaccines.

In one embodiment, the invention includes a molecular backbone or base to which binding molecules (including monoclonal antibodies and fragments such as Fv, Fab, and F(ab')$_2$) may be conjugated. The backbone may be latex, PEG, cellulose, dextran, ficoll, agarose or other polymers. Active groups for cross-linking may be introduced by established methods. Alternatively, long chain peptides containing Lys or Cys residues may be synthesized. A preferred family of amino acid copolymers are synthesized by a routine method, containing Gly, Ser, and Lys (or Cys) at 20:4:1 ratio, with molecular weights of 10,000 to 1,000,000 (about 150 to 15,000 amino acid residues long). Liposomes or microbeads formed by cross-linked polymers such as latex, dextran or agarose, may also be used as the base for conjugating antibody fragments. These liposomes and microbeads are preferably about 1 to 10 μm in diameter and can be suspended homogenously in a liquid medium by agitation.

Any of these conjugates of the invention can also be used diagnostically, to determine the number or proportion of T cells in a fluid sample. For this use, the conjugates of the invention can be used in standard lymphocyte proliferation assays, such as an [$^3$H]-thymidine incorporation assay.

DETAILED DESCRIPTION OF MAKING AND USING THE INVENTION

As noted above, the immunoregulatory substances of the invention include conjugates which have a polymeric backbone, such as latex, polyethylene glycol ("PEG"), cellulose, dextran, ficoll, agarose, an amino acid copolymer, a liposome, or a microbead that is coupled with binding molecules, for example, antibodies or antibody-derived fragments, e.g., Fv, Fab, or F(ab')$_2$, which bind to monovalent antigenic epitopes on CD3, epitopes of the T cell receptor, or other antigens on the surface of T cells, e.g., CD2, CD4, CDs, CD8, or CD28, or wherein at least one of the binding molecules specifically targets one of the antigens on T cells, e.g., CD2, CD3, CD4, CD5, CD8, CD28, or an epitope of the T cell receptor, and other binding molecule(s) specifically target the same antigen or other antigens or epitopes on T cells.

The conjugates preferably include monoclonal antibodies which target T cells, for example, anti-CD3 monoclonal antibodies such as OKT3 (Ortho Diagnostic Systems, Raritan, N.J.), or the monoclonal antibody 64.1 (Hansen, J. A. et al., "Leukocyte Typing", ed. Bernard, A. et al., Springer-Verlag Pulications, Berlin 1984), which has a higher affinity for CD3 than OKT3. Fragments of these antibodies can also be used.

Other monoclonal antibodies specific for the various surface antigens on T cells can be made by standard techniques, using either whole T cells or peptides representing the surface antigens as immunogens. These immunogens can be used to immunize rats, mice, primates (or even another human being). The resulting B cells, or the hybridomas which result following fusion of the B cells with myeloma cells, can be screened against the peptides to isolate the cells of interest. A preferred protocol for preparing monoclonal antibodies is to fuse immune spleen cells of mice with non-secreting mouse myeloma cells, such as NS-1 or SP2/0 cells, using polyethylene glycol.

A preferred immunization protocol for preparing monoclonal antibodies is to inject into each mouse 50 μg of the conjugate of keyhole limpet hemocyanin and the synthetic peptides in complete Fruend's adjuvant. Two and four weeks later, the same amount of antigen is given subcutaneously in incomplete Fruend's adjuvant. After about six weeks, the fourth antigen injection is given intraperitoneally in saline. Mice are sacrificed 4 days after the last injection and the spleens are removed for preparing single cell suspensions for fusion with myeloma cells.

Generally, monoclonal antibodies which are first obtained will be animal-derived, and thus may be immunogenic or allergenic in human therapy. It is therefore desirable to produce humanized antibodies, which can be chimeric in nature (having an animal variable region and a human constant region), or reshaped (having animal hypervariable regions and human framework variable regions and human constant regions). See Riechmann, L. et al., *Nature* 332:323–327 (1988); U.S. Ser. No. 07/952,802 now abandoned. One can also use human genomic expression libraries (Stratagene Corp., La Jolla, Calif.) to produce fragments of human antibodies ($V_H$, $V_L$, $F_V$, Fd, Fab, or F(ab')$_2$). Further, one can create single peptide chain antibodies in which the heavy and light chain Fv regions are connected. See Huston, J. S. et al., *Proc. Natl. Acad. Sci.* USA 85:5879–5883 (1983).

All of the wholly and partially human antibodies are less immunogenic than mammalian equivalents, and the fragments and single chain antibodies are less immunogenic than whole antibodies. All these types of antibodies are therefore less likely to evoke an undesirable immune or allergic response against the antibody portion of the conjugate.

The Fv fragments of the MAbs may be produced in bacteria using single chain antibody technology, as described in U.S. Pat. No. 4,946,778 and International Application No. WO88/09344. The Fv may also be genetically engineered to contain glycosylation sites and produced in mammalian cells, to result in a fragment containing carbohydrate moieties.

The Fab or F(ab')$_2$ may be produced by enzymatic cleavage of whole IgG which is produced by a hybridoma or a transfected cell lines (a myeloma or a cell line such as CHO), using pepsin and papain digestion, respectively.

The Fab or F(ab')$_2$ fragments may be wholly animal or human derived, or they may be in chimeric form, such that the constant domains are derived from the constant regions of human immunoglobulins and the variable regions are derived from the parent murine MAb. Alternatively, the Fv, Fab, or F(ab')$_2$ may be humanized, so that only the complementarity determining regions (CDR) are derived from an animal MAb, and the constant domains and the framework regions of the variable regions are almost entirely of human origin. These chimeric and humanized fragments are less immunogenic than their wholly animal counterparts, and thus more suitable for in vivo use, especially over prolonged periods.

Methods of making chimeric and humanized antibodies are well known in the art, (see, e.g., U.S. Pat. No. 4,816,567, International Application No. WO84/03712, U.S. patent application Ser. No. 07/952,802). The Fv, Fab, or F(ab')$_2$ fragments may be produced from such chimeric or humanized antibodies using proteolytic digestion, as described above.

The antibody fragments can be conjugated to the linear or cross-linked backbone of a liposome using conventional techniques. See, e.g., Ostro, M. J. (Ed.), Liposomes: from Biophysics to Therapeutics (Marcel Dekker, New York, 1987). One preferred method of preparing liposomes and conjugating immunoglobulins to their surface is described by Ishimoto, Y. et al., J. Immunol. Met. 75:351 (1984). Multilamillar liposomes composed of dipaimitoylphosphatidylcholine, cholesterol and phosphotidylethanolamine are prepared. Purified fragments can then be coupled to the phosphatidylethanolamine by the cross-linking agent N-hydroxysuccinimidyl 3-(2-pyridyldithio) propionate. The coupling of the fragment to the liposome can be demonstrated by the release of a pre-trapped marker, e.g., carboxyfluorescence, from the liposomes upon the treatment of secondary antibody against the conjugated fragment and complement. Liposomes have different sizes, ranging from 0.1 to 5 $\mu$m in diameter.

The antibody fragments may also be coupled to microbeads. These microbeads are preferably about 1 to 10 $\mu$m in diameter (i.e., equal to or smaller than the diameter of resting blood lymphocytes), which allows them to be suspended in a liquid medium suitable for pharmaceutic administration in vivo. When agitated, the microbead suspension remains homogenous for at least several minutes, allowing time for withdrawal of the suspension and administration of it to a patient. The SEPHAROSE 4B beads used for immobilizing anti-CD3 antibodies for in vitro studies of T cell activation (Williams, J. M. et. al., J. Immunol. 135:2249 (1985)) are about 45–165 $\mu$m in diameter. These large SEPHAROSE 4B beads settle readily, and do not remain suspended for a sufficient period to allow withdrawal and administration of a homogenous suspension. Also, the beads are so large that they can not pass through the bore of needles of smaller diameters (or higher guage numbers), and, when injected i.v., they may not pass capillaries and may block blood flow in tissues. For in vivo administration, the preferred microbeads should be stable for relatively long periods. Such microbeads include those made by cross-linking, in a well-established manner, latex, agarose or dextran, one example of which is SUPEROSE 12 (Pharmacia LKB Biotechnology, Piscataway, N.J. 08854), and another example of which is glutaraldehyde modified latex beads (Interfacial Dynamics Corporation, Portland, Oreg.).

The antibodies or fragments may be coupled to the liposome, the microbead, or another carrier of the invention, via their carbohydrate moieties. Provided that the carbohydrate moiety is not in the hypervariable region or at the antibody binding sites, the conjugation via the cross-linking with the carbohydrate will not affect binding, as the binding sites will still be available to bind to cell surface antigens.

One preferred way to couple antibodies or fragments of the invention (other than Fv) to a polymer backbone, a liposome, or a microbead is to conjugate them through the carbohydrate moiety on the constant regions. For most antibodies, the carbohydrate side chains are on the Fc portion of the antibody molecule. This will maximize the binding sites which are available and not hindered for binding to the antigens. The conjugation through the Fc will also hamper the antibody's ability to effect ADCC and complement-mediated cytolytic mechanisms, which is desirable for carrying out the purposes of the invention. As another alternative for use in the invention, antibody molecules with site-specific mutations in the Fc region, so that they do not effect ADCC or complement mediated cytolysis or do not do so to any substantial extent, can be prepared. Alegre, M. L. et al., J. Immunol. 148:3461–68 (1992). These modified antibody molecules are also acceptable for use in the invention.

Methods for derivatizing sugar ring moities to create hydrazide groups for coupling with fragments (and antibodies) have been established. See Rodwell, J. D. et al., Proc. Natl. Acad. Sci. U.S.A. 83:2632 (1986). Several immunoconjugates prepared in this way are in clinical studies or pending approval for routine clinical uses.

The polymers for conjugating to the antigen binding sites can be modified to generate active groups for coupling according to established methods. For example, PEG can be derivatized by 1,1'-carbonyldiamidazole to form imidazole carbamate active groups, which react with amino groups of proteins. Beauchamp, C. O. et al., Anal. Biochem. 131:25 (1983). Similar reactions can be used for derivatizing agarose. Bethell, G. S. et al., J. Biol. Chem. 254:2572 (1979). The latex beads which are purchased from Interfacial Dynamics Corporation (Portland, Oreg.) are pre-modified to contain activated groups for coupling with proteins.

The antibodies and fragments can be coupled directly to the derivatized, activated polymers. Bifunctional cross-linkers suitable for conjugating the activated polymers (or liposomes or microbeads) and the antibodies or fragments, can be selected based on the properties desired and the specific substances to be cross-linked. These heterobifunctional reagents are available from several commercial sources, e.g., Pierce Chemical Co., Rockford, Ill., and the reaction procedures are well-known.

The substances of the invention, in appropriate pharmaceutical vehicles, may be administered intravenously (i.v.), so that they can reach the T cells in circulation, spleen, liver, and various lymph nodes. The substances of the invention may also be given intraperitoneally (i.p.), where they will mainly interact with cells in the peritoneal cavity and will be delivered to other lymphoid tissues through the lymphoid circulation. The T cells which are activated and expanded in the spleen and peritoneal cavity may also migrate to different tissues.

The substances of the invention may also be injected directly into or near the solid tumors, warts, or other affected tissues. In this case, the local T cells will be activated and expanded and mediate various immune mechanisms efficiently.

Certain substances of the invention may only induce the activation of resting lymphocytes and not their proliferation. In such case, their administration may be followed by T cell growth factors, such as IL-1, IL-2, or IL-4.

The substances of the invention may be given alone, or in combination with surgery, irradiation treatment, or chemotherapy for cancer patients, or in combination with viral antibiotics or other anti-viral substances for patients with infectious diseases. Certain of the substances of the invention may be given as adjuvants for vaccines or infectious diseases.

The dosage to be administered is determined from the animal model experiments described below. In mice, it was shown that a dose of 16 $\mu$g of whole anti-CD3 IgG coupled to latex beads was well tolerated, as was a dose of 25 $\mu$g of an F(ab')$_2$ fragment of anti-CD3 coupled to latex beads. A tolerable dosage for humans can be approximated by multiplying the animal dose by the ratio of the weight of a human being over that of a mouse.

Among the surface molecules that are involved in the regulation of the activities of lymphocytes, the most important are the components or molecules associated with the TCR on T cells. These antigen receptors interact with antigens or antigen-presenting cells, and respond to antigen stimulation by causing the cell to undergo a sequence of activation, clonal expansion, and differentiation. The activation and expansion of lymphocytes consequently leads to various immune reactions and responses.

The structure of the TCR complex is complicated, and has not yet been not fully characterized, despite extensive study. The information available indicates that the "complete" TCR complex contains one $\alpha$ a chain, one $\beta$ chain, one $\gamma$ chain, one $\epsilon$ chain, one $\delta$ chain, and a homodimer $\zeta$ chain. The $\alpha$ and $\beta$ chains are clonally different and $\alpha/\beta$ dimer is customarily referred to as the TCR. The remaining components of the TCR complex ($\gamma$, $\epsilon$, $\zeta$, and $\delta$ chains) are not polymorphic and are referred to as the CD3 antigen.

It is known that T cells at different differentiation stages or with different functions express different sets of the chains. See e.g., Baniyash, M. et al., *J. Immunol.* 263:9874 (1988); Geisler, C. et al., *J. Immunol.* 145:1761 (1990). Thus, within the TCR complex on most T cells, the antigenic epitopes recognized by most MAbs are monovalent (one single epitope per complex).

Animal model experiments, described below in the example, demonstrate that the conjugates of the invention are therapeutically efficacious in vivo.

EXAMPLE 1

Conjugates of the Invention as In Vivo Immune Enhancers in an Animal Model System Conjugates of the invention were made by conjugating whole IgG molecules or F(ab')$_2$ fragments of the hamster monoclonal antibody 145-2C11, which is specific for murine CD$^3$-$\epsilon$ chain, onto latex microbeads. The latex beads (of a uniform 2.5 $\mu$m diameter) were glutaraldehyde modified and were purchased from Interfacial Dynamics Corporation (Portland, Oreg.). These beads were already modified to contain activated groups for coupling with proteins. Suspensions of these beads could be made homogeneous and suitable for injection with gentle shaking. 5 $\mu$g of 145-2C11.IgG, or 3 $\mu$g of 145-2C11.F(ab')$_2$ were conjugated onto 1 mg of the activated latex beads.

The constructs of 145-2C11.IgG/latex beads (abbreviated as "X.IgG/beads") and 145-2C11.F(ab')$_2$/latex beads ("XF(ab')$_2$/beads") were shown to be as effective as free 145-2C11 (abbreviated as "X.IgG") in inducing the proliferative response of mouse spleen cells in a 3-day in vitro assay. Unconjugated, plain beads and the fragment 145-2C11.F(ab')$_2$ (abbreviated as "X.F(ab')$_2$") did not have significant effects on the proliferative response.

Various amounts of X.IgG/beads and X.F(ab')$_2$/beads were injected via the tail vein into adult BALB/c mice and their effects on the general physiology and the immune system of these mice were compared with those of mice injected with soluble X.IgG, X.F(ab')$_2$, and plain beads. The 65 mice receiving one injection of 4 to 16 $\mu$g of soluble X.IgG experienced a transient increase in spleen size which was evident 72 hours after the injection (day 3). By day 5, the spleens of these mice had begun to lose weight. The mice appeared feeble and lethargic as early as day 1 and lost 30 to 40% of their body weights by day 10. Ten of these 65 mice died, all within 4 days of the injection. The numbers of cells in the spleens of these mice that could be released by mechanically disrupting the spleens' connective tissue increased by 20–30% by day 3 and decreased to 40 to 60% of the normal levels by day 7. To a large extent, the decrease in the total spleen cells could be attributed to the loss of T cells, which were measured with a fluorescence flow cytometric method using a fluorescein isocyanate-labeled anti-Thy-1.2 antibody. In a normal mouse, T cells account for 25–35% of spleen cells. In the mice treated with X.IgG, T cells accounted for about 10% of the spleen cells on day 7. The T cells in the spleens of the treated mice remained at these low levels until day 10, and thereafter, increased, but still did not reach normal levels, even by day 14.

The mice that received one injection of up to 25 $\mu$g of soluble X.F(ab')$_2$ did not show signs of adverse effects. Their physical appearance was normal and their body weight was normal. None died. The total numbers of cells and the proportions of T cells in their spleens were not changed. These observations were consistent with the in vitro results that X.F(ab')$_2$ could not induce T cell activation and proliferation. Similarly, the mice that received one injection of unconjugated, plain latex beads at amounts up to 5 mg did not show any signs of abnormality.

In contrast, whole IgG or F(ab')$_2$ of 145-2C11 conjugated to latex microbeads (X.IgG/beads and X.F(ab')$_2$/beads) had the same effects as free 145-2C11.IgG (X.IgG) on stimulating the splenic T cells in the first 3 days. However, the bead conjugates had drastically different effects on the spleen T cells after day 3 and on the well being of the mice, as early as day 1. The mice receiving one intravenous injection of X.IgG/beads or X.F(ab')$_2$/beads, at up to 16 $\mu$g X.IgG and 25 $\mu$g X.F(ab')$_2$, respectively, developed an activated and expanded immune system. The spleen enlargement, as measured by weight or by the number of cells recovered from minced spleens, was noticeable by day 3, continued to increase until day 5 or day 6, and, thereafter, the spleens returned gradually to normal size by around day 10. The proportion of T cells in the spleens increased from 25–35% to 30–50%. Among these T cells, the proportions of activated T cells, as identified by the expression of interleukin-2 receptors on the cell surface using anti-CD25 and flow cytometry, increased dramatically from 4–6% to 13–21% by day 3.

All of the 123 mice injected with X.IgG/beads or X.F(ab')$_2$/beads appeared normal. Their agility was normal. They did not lose body weight in the two weeks after injection. None of them died. Pathological examinations revealed enlarged spleens and lymph nodes and no other major abnormal symptoms.

Another set of experiments were also ran in which mice were injected intravenously with 50 $\mu$g of chimeric human/mouse IgE (hu, $\epsilon$,$\kappa$/mu V$_H$, V$_L$) from SE44 cells, alone an together with, respectively, X.IgG, and X.IgG/beads. Mice were also injected intraperitoneally with the chimeric human/mouse IgE together with complete Freund's adjuvant. As controls, beads and X.IgG/beads were also injected intravenously. The murine IgG response was then measured after 14 days.

The mice receiving the X.IgG/beads and chimeric human/mouse IgE had a much stronger IgG antibody response to human IgE than the mice which received only chimeric human/mouse IgE. The response of the mice receiving X.IgG/beads and chimeric human/mouse IgE was comparable to that of the mice receiving chimeric human/mouse IgE and complete Freund's adjuvant. Mice receiving soluble X.IgG with chimeric human/mouse IgE did not make a detectable antibody response, nor did mice receiving only the X.IgG/beads or only the beads.

In summary, these studies indicate that T cells and the immune system can be stimulated without T cell depletion in vivo by properly modified anti-CD3 antibodies.

As noted above, the invention is not limited to anti-CD3 antibodies and fragments, but also includes binding molecules, fragments (and conjugates thereof) which are specific for surface antigens of human T lymphocytes, and which have immunoregulatory activities in vivo, when administered according to the techniques of the invention. As is true for anti-CD3, many of these in vivo effects would not be predicted from the known in vitro effects or the in vivo effects with the whole antibodies. The desirable stimulatory effects of such products, that are prepared according to the present invention, will result even though the in vivo effects of IgG specific for T cells are primarily cytolytic effects mediated by complement, ADCC, or other cytolytic mechanisms. In addition to anti-CD3, other examples of antibodies which initiate these cytolytic effects in vivo are anti-CD4 antibodies, Alters, S. E., et al., *J. Immunol.* 144:4587 (1990). All of these antibodies cause T cell depletion in vivo.

Anti-CD4 has been found to have stimulatory effects in vitro. This indicates that, like anti-CD3, when formulated into conjugates of the invention, they would activate or modulate their respective target cells in vivo. A number of studies have indicated that the activation of T cells with an anti-CD3 MAb can be enhanced by an MAb which is specific for a different surface antigen on T cells. These auxiliary MAbs include those specific for HLA class-1 antigens, HLA class-II antigens (such as Ia), CD2, CD4, CD5, CD8, CD28, or CD37. Ceuppens, J. L. et al., *J. Immunol.* 137:1816 (1986); Tutt, A. et al., *J. Immunol.* 147:60 (1991). Thus, the binding molecules which target these antigens, whether used in separate conjugates or in combination with conjugates which include anti-CD3 binding molecules, may be conjugated to microbeads or polymers and used as conjugates of the invention. Some of these antigens, such as CD2, CD4, CD5, and CD8 are specifically expressed by T cells or subsets of T cells. Thus, in one embodiment of the invention, an anti-CD3 binding molecule and an anti-CD2, anti-CD4, anti-CD5, anti-CD8, anti-CD28 or other binding molecule specific for T cells, is conjugated to a polymer backbone, a liposome, or a microbead. The polymerized or immobilized pairs of binding molecules can then be used to activate T cells in vivo.

It should be understood that the terms and expressions described herein are exemplary only and not limiting, and that the scope of the invention is defined only in the claims which follow, and includes all equivalents of the subject matter of those claims.

What is claimed is:

1. A method of increasing activation or proliferation of T cells without causing immunosuppression comprising administering a molecular conjugate having a polymer backbone or microbead coupled with a plurality of binding molecules, each being specific for an antigen on a T cell, and each lacking an Fc portion.

2. The method of claim 1 wherein the antigen on the T cell is CD3, and the polymer backbone is a microbead.

3. The method of claim 2 wherein the microbead is a glutaraldehyde modified latex microbead.

4. The method of claim 1 wherein the binding molecule is selected from the group consisting of Fv, Fab, and $F(ab')_2$ fragments thereof.

5. The method of claim 4 wherein the antigen on the T cell is CD3, and the polymer backbone is a microbead.

* * * * *